US008609630B2

(12) United States Patent
Brown

(10) Patent No.: US 8,609,630 B2
(45) Date of Patent: *Dec. 17, 2013

(54) VITAMIN B12 COMPOSITIONS

(71) Applicant: Bebaas, Inc., Carlsbad, CA (US)

(72) Inventor: Chad Brown, Carlsbad, CA (US)

(73) Assignee: Bebaas, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/759,913

(22) Filed: Feb. 5, 2013

(65) Prior Publication Data

US 2013/0149255 A1 Jun. 13, 2013

Related U.S. Application Data

(63) Continuation of application No. 13/725,745, filed on Dec. 21, 2012, which is a continuation-in-part of application No. 11/219,794, filed on Sep. 7, 2005, now abandoned.

(51) Int. Cl.
A61K 31/70 (2006.01)

(52) U.S. Cl.
USPC .......................................................... 514/52

(58) Field of Classification Search
USPC .......................................................... 514/52
See application file for complete search history.

(56) References Cited

U.S. PATENT DOCUMENTS

| | | | |
|---|---|---|---|
| 3,425,600 A | 2/1969 | Abplanalp | |
| 3,531,485 A | 9/1970 | Freed | |
| 3,921,637 A | 11/1975 | Bennie et al. | |
| 3,957,795 A | 5/1976 | Kubela | |
| 3,991,761 A | 11/1976 | Cocozza | |
| 4,069,819 A | 1/1978 | Valentini et al. | |
| 4,166,452 A | 9/1979 | Generales, Jr. | |
| 4,249,526 A | 2/1981 | Dean et al. | |
| 4,256,108 A | 3/1981 | Theeuwes | |
| 4,265,874 A | 5/1981 | Bonsen et al. | |
| 4,338,931 A | 7/1982 | Cavazza | |
| 4,432,975 A | 2/1984 | Libby | |
| 4,446,862 A | 5/1984 | Baum et al. | |
| 4,500,515 A | 2/1985 | Libby | |
| 4,525,341 A | 6/1985 | Deihl | |
| 4,627,432 A | 12/1986 | Newell et al. | |
| 4,724,231 A | 2/1988 | Wenig | |
| 4,811,731 A | 3/1989 | Newell et al. | |
| 4,884,565 A | 12/1989 | Cocozza | |
| 4,889,114 A | 12/1989 | Kladders | |
| 4,995,385 A | 2/1991 | Valentini et al. | |
| 5,035,237 A | 7/1991 | Newell et al. | |
| 5,048,514 A | 9/1991 | Ramella | |
| 5,428,023 A | 6/1995 | Russell-Jones et al. | |
| 5,683,997 A | 11/1997 | Buhlmayer | |
| 5,853,753 A | 12/1998 | Maierhofer et al. | |
| 5,936,082 A | 8/1999 | Bauer | |
| 6,089,228 A | 7/2000 | Smith et al. | |
| 6,096,290 A | 8/2000 | Collins et al. | |
| 6,183,723 B1 | 2/2001 | Seetharam et al. | |
| 6,255,294 B1 | 7/2001 | Armstrong et al. | |
| 6,274,564 B1 | 8/2001 | Sarill et al. | |
| 6,726,924 B2 | 4/2004 | Keller | |
| 6,752,986 B2 | 6/2004 | Bauer et al. | |
| 6,849,639 B2 | 2/2005 | Dominguez et al. | |
| 6,894,033 B2 | 5/2005 | Cruz et al. | |
| 6,919,343 B2 | 7/2005 | Wood | |
| 7,067,261 B2 | 6/2006 | Bencherif | |
| 2003/0018009 A1 | 1/2003 | Collings | |
| 2003/0086901 A1 | 5/2003 | Cruz et al. | |
| 2003/0152552 A1 | 8/2003 | Cruz et al. | |
| 2003/0199424 A1 | 10/2003 | Smith | |
| 2004/0097565 A1 | 5/2004 | Terashita et al. | |
| 2004/0162292 A1 | 8/2004 | Evenstad et al. | |
| 2004/0180941 A1 | 9/2004 | Hepworth | |
| 2004/0192729 A1 | 9/2004 | Rudolf | |
| 2006/0024241 A1 | 2/2006 | Brown | |
| 2007/0053930 A1 | 3/2007 | Brown | |
| 2007/0178141 A1 | 8/2007 | Brown | |
| 2007/0225250 A1 | 9/2007 | Brown | |
| 2013/0131007 A1 | 5/2013 | Brown | |

FOREIGN PATENT DOCUMENTS

| | | |
|---|---|---|
| EP | 0467172 A1 | 1/1992 |
| EP | 0469814 A1 | 2/1992 |
| EP | 1773354 | 4/2007 |
| EP | 1933851 | 6/2008 |
| JP | 2002/533399 | 10/2002 |
| JP | 2005/513010 | 5/2005 |
| KR | 2004/0065979 A | 7/2004 |

(Continued)

OTHER PUBLICATIONS

Liu et al, "Metformin-related vitamin B12 deficiency", Age Ageing (Mar. 2006), 35 (2), pp. 200-201.*
Response to Non-Final Office Action filed in U.S. Appl. No. 11/219,794 dated Feb. 29, 2008.
Response to Non-Final Office Action Filed in U.S. Appl. No. 11/219,794 dated Jan. 24, 2011.
Response to Non-Final Office Action Filed in U.S. Appl. No. 11/219,794 dated Dec. 11, 2009.
Amendment After Final Office Action Filed in U.S. Appl. No. 11/219,794 dated Feb. 13, 2012.
Amendment After Final Office Action Filed in U.S. Appl. No. 11/219,794 dated Mar. 15, 2012.
Best Declaration under 37 CFR 1.132 dated Jan. 8, 2010, submitted in U.S. Appl. No. 11/219,794 on Feb. 1, 2010.
Best Declaration under 37 CFR 1.132 dated Jul. 25, 2011, submitted in U.S. Appl. No. 11/219,794 on Sep. 29, 2011.
Best Declaration under 37 CFR 1.132 dated Mar. 17, 2011, submitted in U.S. Appl. No. 11/219,794 on Sep. 29, 2011.
Arcangelo, V.P., et al., *Pharmacotherapeutics for advanced practice : a practical approach*, 2nd Edition, 2006, p. 17.

(Continued)

Primary Examiner — Elli Peselev
(74) Attorney, Agent, or Firm — Wilson, Sonsini, Goodrich & Rosati

(57) ABSTRACT

This disclosure provides compositions of vitamin $B_{12}$, and methods of treatment or amelioration of a disease associated with vitamin $B_{12}$ deficiency. The composition can take the form of a solid, semi-solid, gummy, or chewable lozenge. The composition can also take the form of a troche, a candy, a wafer, an orally disintegrating tablet, a sublingual tablet, a buccal tablet, a buccal patch, an oral dissolvable film, an aerosol or spray, a lip balm, and chewing gum.

13 Claims, No Drawings

(56) References Cited

FOREIGN PATENT DOCUMENTS

| WO | WO 86/05987 A1 | 10/1986 |
|---|---|---|
| WO | WO 90/07351 A1 | 7/1990 |
| WO | WO 91/02558 A1 | 3/1991 |
| WO | WO 92/00584 | 1/1992 |
| WO | WO 92/20661 | 11/1992 |
| WO | WO 93/09832 A1 | 5/1993 |
| WO | WO 93/20816 | 10/1993 |
| WO | WO 94/08522 A1 | 4/1994 |
| WO | WO 94/13646 | 6/1994 |
| WO | WO 94/23378 | 10/1994 |
| WO | WO 94/28896 | 12/1994 |
| WO | WO 95/00498 | 1/1995 |
| WO | WO 95/22525 | 8/1995 |
| WO | WO 96/09085 | 3/1996 |
| WO | WO 99/07413 | 2/1999 |
| WO | WO 00/20398 | 4/2000 |
| WO | WO 01/19344 A1 | 3/2001 |
| WO | WO 01/82916 | 11/2001 |
| WO | WO 02/05799 | 1/2002 |
| WO | WO 02/40008 | 5/2002 |
| WO | WO 02/057264 | 7/2002 |
| WO | WO 02/060923 | 8/2002 |
| WO | WO 02/100429 | 12/2002 |
| WO | WO 03/000010 A2 | 1/2003 |
| WO | WO 03/20816 | 3/2003 |
| WO | WO 03/041701 | 5/2003 |
| WO | WO 03/064414 | 8/2003 |
| WO | WO 03/066577 | 8/2003 |
| WO | WO 03/077912 | 9/2003 |
| WO | WO 03/097024 | 11/2003 |
| WO | WO 03/099279 | 12/2003 |
| WO | WO 03/101381 | 12/2003 |
| WO | WO 2004/006959 | 1/2004 |
| WO | WO 2004/024061 | 3/2004 |
| WO | WO 2004/099248 | 11/2004 |
| WO | WO 2006/020291 | 2/2006 |
| WO | WO 2007/030108 | 3/2007 |
| WO | WO 2007/087631 | 8/2007 |

OTHER PUBLICATIONS

The Mouth, Gray's Anatomy of the Human Body, 20$^{th}$ Edition, from Yahoo! Education [online] 2009 [retrieved on Feb. 10, 2012]. Retrieved from the internet: http://education/yahoo.com/reference/gray/subjects/subject/242.
Best Supplemental Declaration under 37 CFR 1.132 dated Mar. 15, 2012, submitted in U.S. Appl. No. 11/219,794 on Mar. 15, 2012.
Amendment Entered with Filing of RCE Filed in U.S. Appl. No. 11/219,794 dated May 1, 2009.
Amendment Entered with Filing of RCE Filed in U.S. Appl. No. 11/219,794 dated Apr. 11, 2012.
Amendment After Notice of Appeal Filed in U.S. Appl. No. 11/219,794 dated May 25, 2010.
Amendment After Notice of Appeal Filed in U.S. Appl. No. 11/219,794 dated Sep. 29, 2011.
Supplemental Response Filed in U.S. Appl. No. 11/219,794 dated Feb. 1, 2010.
Dagnelie, et al., "Vitamin B-12 from algae appears not to be bioavailable," Am. J. Clin. Nutr., (1991), vol. 53, pp. 695-697.
"Methylcobalamin", Alternative Medicine Review: vol. 3(6): pp. 461-463; (1998).
Astier et al., "Simultaneous Determination of Hydroxocobalamin and its Cyanide Complex . . . "; Journal of Chromatography B: Biomedical Science . . . ; (1995); vol. 667, Issue 1; pp. 129-135.
Bachmann, "B-12 (Methylcobalamin), Thorne Article", Mar. 2001.
Bauer, et al.; "Effects of Interferon B on Transcobalamin II-Receptor Expression . . . "; 2002; Journal of the National Cancer Institute vol. 94, No. 13; pp. 1010-1019.
Bhat, "The Journal of Allergy and Clinical Immunology" (including Allergy Abstracts), vol. 79(1): pp. 461-464; (1987).
Bioanalytical Report for "Determination of Hydroxocobalamin in Dog Plasma by LC/MS QTRAP5500"; 2009, pp. 1-11, Non-GLP Study pp. 1-6, and Pharmacokinetic Analysis pp. 1-12.

Borutaite, et al.; "What Else Has to Happen for Nitric Oxide to Induce Cell Death?"; 2005; Biochemical Society; vol. 33, No. 6; pp. 1394-1396.
Broderick, et al., "Nitric Oxide Scavenging by the Cobalamin Precursor Cobinamide"; Journal of Biological Chemistry; (2005); vol. 280, No. 10; pp. 8678-8685.
Broderick, et al., "Nitrosyl-Cobinamide, a New and Direct Nitric Oxide . . . "; Exp Biol Med (2007); vol. 232; pp. 1432-1440.
Brouwer, et al., "Nitric Oxide Interactions with Cobalamins . . . "; 1996; Blood; vol. 88, No. 5; pp. 1857-1864.
Chawla-Sarkar, et al.; "Suppression of NF-κB Survival Signaling by Nitrosylcobalamin."; 2003; Journal of Bio. Chem.; vol. 278, No. 41; Issue of Oct. 10, pp. 39461-39469.
Cooperman, et al.; "Distribution of Radioactive and Nonradioactive Vitamin B12 in the Dog", Journal of Biological Chemistry: vol. 235(1): pp. 191-194; (1960).
Cyanocobalamin-methylcobalamin SL from WebMD [online] 2005-2013 [retrieved on Feb. 8, 2013]. Retrieved from the Internet: http://www.webmd.com/drugs/drug-20179-cyanocobalamin-methylcodalamin+SL.aspx?drugid=20179&drugname=cyanocobalamin-methylcobalamin+SL.
Danishpajooh, et al.; "Nitric Oxide Inhibits Methionine Synthase Activity . . . "; 2001; Journal of Biological Chemistry; vol. 276, No. 29, Issue of Jul. 20, pp. 27296-27303.
EP05773512.8 Search Report dated Apr. 8, 2012.
EP05793864.9 Search Report dated Aug. 27, 2008.
Fujiya, et al., "Methylcobalamin and Diabetic Neuropathy", Clin Ther 1987, vol. 9 No. 2,pp. 183-192.
HVAS, et al., "Diagnosis and Treatment of Vitamin B12 deficiency. An Update"; The Hematology Journal; (2006); vol. 91 No. 11; pp. 1506-1512.
JP Appl. No. 2008-529966 Office Action dated Oct. 11, 2011.
JP Appl. No. 2008-529966 Office Action dated Jun. 15, 2012.
Kelly, Gregory, N.D. "The Coenzyme Forms of Vitamin B12: Toward an Understanding of their Therapeutic Potential," Alternative Medicine Review, vol. 2, No. 6, 1997, pp. 459-471, San Diego, CA.
MX Appl. No. MX/a/2007/001348 Office Action dated Feb. 21, 2012.
Nava-Ocampo, et al., "Pharmacokinetics of High Doses of Cyanocobalamin Administered . . . "; Clinical Pharmacology & Therapeutics; (2004) 75, p. 84; Abstract.
PCT/US2005/025585 Search Report dated Nov. 6, 2006.
PCT/US2005/31628 Search Report dated Jun. 2, 2006.
Priest et al., "Biochemistry," 2004, 43:986-9876.
Rahbar et al., "Biochem. Biophys. Res. Commun ," 1999, 262: 651-656.
Rosenthal, at al., "The Absorption of Cyanocobalamin (Vitamin B12) From the Gastrintestinal Tract of Dogs", Journal of Nutrition: vol. 56; pp. 67-82; (1954).
Sharabi, et al., "Replacement Therapy for Vitamin B12 Deficiency: Comparison between the sublingual . . . ", Journal Clinical Pharmacol: vol. 56: pp. 635-638; (2003).
Takenaka, Shigeo et al., "Feeding Dried Purple Laver (Nor)) to Vitamin B12-Deficient Rats Significantly Improved Vitamin B12 Status," British Journal of Nutrition, vol. 85, pp. 699-703, 2001.
Tang, et al.; "Nitrosylcobalamin Promotes Cell Death via S Nitrosylation . . . "; 2006; Molecular and Cellular Biology; vol. 26, No. 15; pp. 5588-5594.
Taylor, et al., "Nitric Oxide; A Key Regulator of Myeloid Inflammatory Cell Apoptosis.."; 2003; Cell Death and Differentiation; vol. 10; pp. 418-430.
Tiwara, Deepak et al., "In Vitro-In Vivo Evaluation of a Controlled Release Buccal Bioadhesive Device for Oral Drug Delivery," Pharmaceutical Research, vol. 16, No. 11, pp. 1775-1780, 1999.
Tsukerman, et al., "Pharmacokinetics of Hydroxy-, Adenosyl-, and Cyanocobalamins in the Case of Oral Administration to Rats", Plenum Publishing Corp., pp. 585-589.
Tsukerman, et al., "Pharmacokinetics of Methylcobalamin in Rats", Plenum Publishing Corp., 1992, pp. 764-767.

(56) References Cited

OTHER PUBLICATIONS

Walker, et al.;"Induction of Apoptosis in Neoplastic Cells by Depletion of Vitamin B12 "; 1997; Cell Death and Differentiation (1997); vol. 4; pp. 233-241.

Weinberg, et al. "Cobalamins and Cobinamides Inhibit Nitric Oxide . . . "; Blood (ASH Annual Meeting Abstracts); (2005); Abstract 2225; pp. 1-3.

Weinberg, et al "Inhibition of Nitric Oxide Synthase by Cobalamins and Cobinamides"; Fee Radic. Biol. Med. (2009), doi:10.1016/j.freeradbiomed.2009.3.01; pp. 1-7.

Woods; et al.,"Vitamin B12Co60 Distribution in Dog Tissue During Many Months", Journal Exp. Med.: vol. 108(1); pp. 1-8; (1958).

Yamamoto, et al.,"Further Studies on Absorption of Vitamin B12 Following Oral and Parental Administration", Journal of Nutrition: vol. 45: pp. 507-519; (1951).

* cited by examiner

VITAMIN B12 COMPOSITIONS

CROSS REFERENCE TO RELATED APPLICATION

This application is a continuation of U.S. application Ser. No. 13/725,745 filed on Dec. 21, 2012, which is a continuation-in-part of U.S. application Ser. No. 11/219,794 filed on Sep. 7, 2005, both of which are incorporated herein by reference in their entirety.

FIELD OF INVENTION

The present invention provides improved vitamin $B_{12}$ compositions containing a mixture of vitamin $B_{12}$ analogues in effective amounts for enhanced delivery via the mucosal membranes, such as the mouth, nose, etc., to ameliorate any condition associated with vitamin $B_{12}$ deficiency in a human.

BACKGROUND OF THE INVENTION

Vitamin $B_{12}$, otherwise known as cobalamin, is the largest and most structurally complex of the eight water-soluble B vitamins. Vitamin $B_{12}$ is a class of cobalt and corrin ring molecules that possess vitamin activity. The sixth coordination site of the corrin ring is either a cyano group (—CN), a hydroxyl group (—OH), a methyl group (—CH$_3$) or a 5'-deoxyadenosyl group, creating four forms of vitamin $B_{12}$, including, cyanocobalamin, hydroxocobalamin, methylcobalamin, and adenosylcobalamin.

Vitamin $B_{12}$ is synthesized by microbes, but not by humans or plants. Gastrointestinal absorption of vitamin $B_{12}$, from food or supplements, depends on the presence of sufficient intrinsic factor and calcium ions. Adenosylcobalamin and methylcobalamin are the active forms of vitamin $B_{12}$ in humans. Vitamin $B_{12}$ deficiency may result from intrinsic factor deficiency (pernicious anemia), partial or total gastrectomy, or diseases of the distal ileum, intestinal problems and nerve damage, etc. Conditions that make people vulnerable to vitamin $B_{12}$ deficiency include: Crohn's disease, multiple sclerosis, HIV/AIDS, advanced age (>65 years), chronic intestinal inflammation, intestinal surgery, food moving too quickly through the intestine, strict vegetarian diets, excessive alcohol consumption for longer than 2 weeks, long-term use of acid reducing drugs, or drug-therapy associated with anemia.

Vitamin $B_{12}$ has also been used in the treatment of IgE-mediated allergic diseases, such as allergic rhinitis and asthma. Oral ingested vitamin $B_{12}$ is ineffective in the treatment of allergic disease, possibly due to liver metabolism.

Cyanocobalamin (Crystamine, Cyomin, Crysti 1000, Nascobal®) is the most widely sold analogue of vitamin $B_{12}$. Cyanocobalamin is available in injectable (subcutaneous or intramuscular) and oral forms and has the advantage of having a stable shelf life at standard temperature and pressure (STP). Nascobal®, an intranasal gel formulation of cyanocobalamin, has been clinically shown to maintain adequate serum levels of vitamin $B_{12}$. The nasal gel can be self-administered through a nasal delivery system that avoids the discomfort of intramuscular injections of $B_{12}$.

Since vitamin $B_{12}$ is very large, orally ingested cyanocobalamin is improperly digested and only small amounts of the vitamin get absorbed by the host. The drawback of the injectable form is that it is invasive, expensive, and inconvenient. Hence, there is a need for more effective forms of vitamin $B_{12}$ that can be absorbed more easily to ameliorate conditions associated with vitamin $B_{12}$ deficiency.

SUMMARY OF THE INVENTION

Many patients require vitamin $B_{12}$ supplementation to combat vitamin $B_{12}$ deficiency associated with anemia, pernicious anemia, immune system disorders, nerve damage, partial removal of the stomach or small intestine, or administration of drugs known to impair vitamin $B_{12}$ absorption. Because of the large size of vitamin $B_{12}$, the body neither efficiently metabolizes nor absorbs the vitamin. Existing vitamin $B_{12}$ compositions fail to provide convenient self-administration for patients in a readily absorbable form. These patients often rely on professionally administered vitamin $B_{12}$ injections, which are invasive, painful, expensive, and inconvenient. Accordingly, provided herein are compositions, methods, and kits that offer superior absorbability and administration compared to currently available vitamin $B_{12}$ treatments.

Disclosed herein, in certain embodiments, are compositions, comprising: (a) cyanocobalamin, hydroxocobalamin, methylcobalamin in substantially equivalent ratios; and (b) a carrier suitable for forming a solid or semi-solid carrier matrix. In some embodiments, the carrier is a sugar, sugar alcohol, polyethylene glycol (PEG), starch, gum, polymer, or combination thereof. In some embodiments, the carrier comprises isomalt, a PEG, or a combination thereof. In some embodiments, the PEG is PEG-8000. In some embodiments, the carrier comprises PEG-8000, and isomalt, or a derivative thereof. In some embodiments, the compositions further comprise a lubricant. In some embodiments, the lubricant is magnesium stearate. In some embodiments, the compositions further comprise a flavoring agent. In some embodiments, the flavoring agent is: apple, almond, amaretto, anise, apricot, banana, banana orange, blackberry, black cherry, black currant, black walnut, blueberry, brandy, bubblegum, butter rum, butterscotch, caramel, cinnamon, citrus, citrus punch, cherry, chocolate, chocolate banana pie, chocolate covered cherry, chocolate hazelnut, cloves, coconut, coffee, cotton candy, crème de menthe, egg nog, English toffee, ginger, grape, grapeade, grape bubblegum, grapefruit, fig, hazelnut, honey, Irish cream, kiwi, lavender, lemon, licorice, lime, maple, marshmallow, mint, mocha, molasses, orange, orange cream, passion fruit, peach, pecan, peppermint, pina colada, pineapple, pistachio, plum, praline, pomegranate, pumpkin, raspberry, red licorice, root beer, sassafras, sour apple, spearmint, strawberry, strawberry cream, tangerine, tropical fruit, tutti-fruiti, vanilla, walnut, watermelon, white chocolate, wild cherry, or wintergreen. In some embodiments, the flavoring agent is cherry. In some embodiments, the composition is formulated as a lozenge, a candy, a wafer, a tablet, a patch, a film, a spray, a lip balm, or gum. In some embodiments, the composition is formulated as a lozenge. In some embodiments, the cyanocobalamin, hydroxocobalamin, and methylcobalamin, together, comprise about 1.2% wt/wt of the composition. In some embodiments, the compositions comprise substantially equivalent ratios of cyanocobalamin, hydroxocobalamin, and methylcobalamin, as well as isomalt, polyethylene glycol, flavoring, and magnesium stearate.

Disclosed herein, in certain embodiments, is a method for treating or ameliorating vitamin $B_{12}$ deficiency in a human in need thereof, comprising: administering to the human a composition comprising (a) methylcobalamin, hydroxocobalamin, and cyanocobalamin in substantially equivalent ratios, (b) a carrier suitable for forming solid or semi-solid carrier matrix, (c) a flavoring agent, and optionally, (d) a lubricant. In some embodiments, the composition comprises: (a) methylcobalamin, hydroxocobalamin, and cyanocobalamin in substantially equivalent ratios, (b) isomalt, (c) PEG, (d) cherry flavoring, and, optionally, (e) magnesium stearate. In some embodiments, the composition comprises: (a) methylcobalamin, hydroxocobalamin, and cyanocobalamin in substantially equivalent ratios, (b) isomalt, (c) PEG, (d) cherry flavoring, and (e) magnesium stearate. In some embodiments, the vitamin $B_{12}$ deficiency is associated with anemia. In some embodiments, the vitamin $B_{12}$ deficiency is associated with pernicious anemia. In some embodiments, the vitamin $B_{12}$ deficiency is associated with: Graves' disease, hypothyroidism, thyroiditis, vitiligo, Addison's disease, atrophic gastritis, and/or thrombocytopenia. In some embodiments, the vitamin $B_{12}$ deficiency is associated with: amyotrophic lateral sclerosis (ALS), multiple sclerosis (MS), Crohn's disease, Celiac disease, ulcerative colitis, Alzheimer's disease, HIV/AIDS, joint inflammation, and/or arthritis. In some embodiments, the vitamin $B_{12}$ deficiency is associated with the administration of drugs known to impair absorption of vitamin $B_{12}$. In some embodiments, the drug known to impair absorption of vitamin $B_{12}$ is: a gastric acid inhibitor, a biguanide, a proton pump inhibitor, an $H_2$ receptor antagonist, metformin, and/or chloramphenicol. In some embodiments, the drug known to impair absorption of vitamin $B_{12}$ is methotrexate. In some embodiments, the vitamin $B_{12}$ deficiency is associated with ataxia. In some embodiments, the vitamin $B_{12}$ deficiency is associated with partial removal of the stomach or small intestine. In some embodiments, the vitamin $B_{12}$ deficiency is associated with alcoholism. In some embodiments, the hereditary disorder is selected from: Alagille's syndrome, severe methylenetetrahydrofolate reductase deficiency, homocystinuria, and/or transcobalamin deficiency.

Disclosed herein, in certain embodiments, is a kit, comprising: a composition comprising (a) methylcobalamin, hydroxocobalamin, and cyanocobalamin in substantially equivalent ratios, (b) a carrier suitable for forming solid or semi-solid carrier matrix, (c) a flavoring agent, and optionally, (d) a lubricant. In some embodiments, the composition comprises: (a) methylcobalamin, hydroxocobalamin, and cyanocobalamin in substantially equivalent ratios, (b) isomalt, (c) PEG, (d) cherry flavoring, and, optionally, (e) magnesium stearate. In some embodiments, the composition comprises: (a) methylcobalamin, hydroxocobalamin, and cyanocobalamin in substantially equivalent ratios, (b) isomalt, (c) PEG, (d) cherry flavoring, and (e) magnesium stearate. In some embodiments, the kit further comprises instructions for use.

DETAILED DESCRIPTION OF THE INVENTION

Existing vitamin $B_{12}$ compositions fail to provide users with a composition that provides an adequate absorption profile in a conveniently self-administered medium.

Advantages of the compositions, methods, and kits described herein include, but are not limited to, providing a non-invasive medium for vitamin $B_{12}$ self-administration. Additional advantages of the compositions, methods, and kits described herein include, providing a lower cost alternative to traditional vitamin $B_{12}$ administration.

Described herein, in certain embodiments is a composition, comprising: cyanocobalamin, hydroxocobalamin and methylcobalamin in substantially equivalent ratios.

Also described herein in certain embodiments, is a method for treating or ameliorating a disease associated with vitamin $B_{12}$ deficiency, comprising: administering the composition described herein.

Also described herein in certain embodiments, is a kit, comprising: the composition described herein and instructions for use.

Certain Definitions

The following terms used in the specification and claims shall have the following meanings for the purpose of the Application. Unless otherwise defined, all technical terms used herein have the same meaning as commonly understood by one of ordinary skill in the art to which this invention belongs.

As used in this specification and the appended claims, the singular forms "a," "an," and "the" include plural references unless the context clearly dictates otherwise. Any reference to "or" herein is intended to encompass "and/or" unless otherwise stated.

The term "active ingredients or compounds" of the invention refers to cobalamins including, but not limited to, adenosylcobalamin, cyanocobalamin, methylcobalamin, hydroxocobalamin, etc. The active ingredients are used in different mixtures containing varying effective amounts of each active compound of the invention, which would be suitable for the treatment of different types of vitamin $B_{12}$ deficiencies.

The term "mixture" refers to a combination containing different types of active ingredients defined above, in effective amounts, useful for the treatment of vitamin $B_{12}$ deficiency.

The term "effective amount" refers to that amount, which when administered, either alone or in a mixture, is sufficient to effect the treatment of a condition with vitamin $B_{12}$ deficiency.

The term "inert ingredients" refers to components like pharmaceutically acceptable carriers, adjuvant, diluents or excipients, etc., that must be compatible with the other ingredients of the formulation and not deleterious to the recipient thereof.

The term "composition" or a "formulation" as used herein refers to a product comprising the specified active ingredients in the specified amounts, as well as any product which results, directly or indirectly, from the combination of the specified active ingredients in the specified amounts. Such term is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by mixing any active compound of the present invention and a pharmaceutically acceptable carrier.

The phrase "substantially equivalent ratio" means the ratio of one component to another component (for example, the ratio of methylcobalamine to hydroxycobalamin to cyanocobalamin) is the same, plus or minus about 30%, about 25%, about 20%, about 15%, about 10%, about 5%, about 2.5%, about 1%.

The terms "administration of" and/or "administering a" composition refers to providing any composition of the invention, in any formulation, to a human in need of treatment.

The term "buccal" refers to delivery of a drug by passage of the drug through the buccal mucosa into the blood stream.

As used herein, "buccal mucosa" refers to the epithelial membranes lining the mouth, including the cheek and under the tongue (sublingual).

Compositions

Disclosed herein, in certain embodiments, are compositions, comprising: cyanocobalamin, hydroxocobalamin, and methylcobalamin in substantially equivalent ratios. In some embodiments, the composition further comprises a carrier suitable for forming solid or semi-solid carrier matrix. In other embodiments, the composition also comprises a lubricant. In some embodiments, the composition further comprises a flavoring agent.

In some embodiments, the composition comprises a carrier suitable for forming solid or semi-solid carrier matrix. In some embodiments, the carrier is selected from water, sugar or sugar substitutes, sugar alcohol, polyethylene glycol, alcohols, glycerin, oils or phospholipids, proteins, waxes, gums, or polymers.

Examples of suitable sugars include, but are not limited to, granulated sugar, powdered sugar, isomaltulose, lactosucrose, corn syrup, corn syrup solids, high fructose corn syrup, honey, maple syrup, maltodextrin, crystalline-fructose, dextrose, nonpareils, stevia sugar, acesulfame K, aspartame, neotame, saccharin, sucralose, trehalose, tagatose, fructo-oligosaccaride, derivatives thereof, or any combinations thereof.

Examples of suitable sugar alcohols include, but are not limited to, sorbitol, xylitol, maltitol, isomalt, lactitol, mannitol, erythritol, hydrogenated starch hydrosates, derivatives thereof, or any combinations thereof. In some embodiments, the carrier comprises isomalt or a derivative thereof. Exemplary isomalt derivatives include, but are not limited to, galenIQ™ 720, galenIQ™ 721, galenIQ™ 800/810, galenIQ™ 960/980, galenIQ™ 981, and galenIQ™ 990.

Examples of suitable polyethylene glycols (PEGs) include, but are not limited to, PEGs with molecular weights between 900 and 8500, including PEG-1000, -1450, -1500, -2000, -3000, -4000, -5000, -6000, -7000, -8000, derivatives thereof, or any combinations thereof. In some embodiments, the carrier comprises PEG-8000.

Examples of suitable oils and phospholipids include, but are not limited to, mineral oil, essential oil, castor oil, fatty acids, vegetable oils, sweet almond oil, apricot kernel oil, avocado oil, grapeseed oil, hemp seed oil, macadamia oil, olive oil, and sunflower oil, coconut oil, palm oil, mango butter, and shea butter, purified egg or soya lecithins (lecithin E100, lecithin E80 and phospholipons, for example, phospholipon 90), ceramides, hydrogenated phospholipids, phosphatidylethanolamine, phosphatidylglycerol, phosphotidylcholine, phosphatidylserine, dipalmitoylphosphatidylcholine, dipalmitoylglycerophosphatidylcholine, dimyristoylphosphatidylcholine, distearoylphosphatidylcholine, cardiolipin, phosphatidylinositol, glycerophosphocholine, phosphatidic acid, sphingomyelin, derivatives thereof, or any combinations thereof.

Examples of suitable polysaccharides, including, but are not limited to: hydroxypropyl methylcellulose, hydroxypropyl cellulose, hydroxypropyl cellulose ethers, hydroxyethyl cellulose, sodium carboxymethyl cellulose, croscarmellose sodium, methyl cellulose, ethyl cellulose, microcrystalline cellulose, low-substituted hydroxypropyl cellulose, pullulan, dextran, dextrin, levan, elsinan, chitosan, pectins, starches, cellulose acetate phthalate, cellulose acetate butyrate, amylase starch, hydroxypropylated high amylase starch, sodium alginate, alginic acid, carboxymethyl cellulose, derivatives thereof, or any combinations thereof.

Examples of suitable proteins include, but are not limited to, collagen, zein, soy protein isolate, whey protein isolate, gluten, casein, gelatin, derivatives thereof, or any combinations thereof.

Examples of suitable waxes, include, but are not limited to: lanolin, beeswax, candelilla wax, carnuba wax, rice wax, ouricurry wax, esparto grass wax, cork fibre wax, sugarcane wax, microcrystalline waxes, paraffins and ozokerite, polyethylene waxes, olefin wax, silicone-modified olefin wax, derivatives thereof, or any combinations thereof.

Examples of suitable gums, include, but are not limited to: xanthan gum, tragacanth gum, acacia gum, arabic gum, gellan gum, carrageenan, locust bean gum, guar gum, derivatives thereof, or any combinations thereof.

Examples of suitable polymers, include, but are not limited to: vinyl polymers and copolymers, acrylic acid polymers and copolymers, polyethylene oxides, polyacrylates, polyvinylpyrrolidone, polyvinyl alcohol, HPMC K15, 5-methylpyrrolidinone chitosan, derivatives thereof, or any combinations thereof.

Exemplary additional carriers that may be used with the compositions disclosed herein include, but are not limited to, glycerin, silicone, petroleum jelly, petrolatum, parabens, derivatives thereof, or any combinations thereof.

In some embodiments, the carrier comprises an isomalt and PEG-8000.

In some embodiments, the lubricant is selected from: magnesium stearate, calcium stearate, stearic acid, sodium stearylfumarate, talc, hydrogenated vegetable oils and polyethylene glycol. In some embodiments, the lubricant is magnesium stearate.

In some embodiments, the flavoring agent is selected from: synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2

(berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, mixtures thereof and the like.

In some embodiments, the compositions further comprise antimicrobial agents, plasticizing agents, sulfur precipitating agents, saliva stimulating agents, cooling agents, surfactants, stabilizing agents, emulsifying agents, thickening agents, binding agents, coloring agents, sweeteners, fragrances, and the like. Exemplarily sulfur precipitating agents useful in the present invention include metal salts such as copper salts (e.g., copper gluconate) and zinc salts (e.g., zinc citrate and zinc gluconate). Exemplarily saliva stimulating agents include, but are not limited to food acids such as citric, lactic, malic, succinic, ascorbic, adipic, fumaric and tartaric acids.

The weight ratio of the respective ingredients may be varied when necessary and will depend upon the effective dose of each ingredient or the effective dose of the combination of all the active ingredients in a formulation. Generally, an effective dose of each will be used. In a particularly preferred embodiment, a combination of active ingredients is used in the composition, for example, methylcobalamin, hydroxocobalamin, and cyanocobalamin. In a preferred embodiment, a combination of active ingredients is used in the composition, for example, adenosylcobalamin: hydroxocobalamin: cyanocobalamin. Generally, the active ingredients occur as substantially equivalent ratios. In some embodiments, the composition comprises substantially equivalent ratios of methylcobalamin, hydroxocobalamin, and cyanocobalamin. Alternatively, in some embodiments, the composition comprises substantially equivalent ratios of adenosylcobalamin, cyanocobalamin, and hydroxocobalamin. The amount of adenosylcobalamin and hydroxocobalamin advantageously will generally range from 250-750 µg, while the range for cyanocobalamin will generally range from 1500-2500 µg in a 3 mg cobalamin formulation. Other combinations of active ingredients of the present invention are also possible as is understood in the art.

In some embodiments, a composition disclosed herein comprises, by way of non-limiting example, 0.5%-2.0%, 0.6%-2.0%, 0.7%-2.0%, 0.8%-2.0%, 0.9%-2.0%, 1.0%-2.0%, 1.1%-2.0%, 1.2%-2.0%, 1.3%-2.0%, 1.4%-2.0%, 1.5%-2.0%, 1.6%-2.0%, 1.7%-2.0%, 1.8%-2.0%, 1.9%-2.0%, 0.5%-0.6%, 0.5%-0.7%, 0.5%-0.8%, 0.5%-0.9%, 0.5%-1.0%, 0.5%, 1.1%, 0.5%-1.2%, 0.5%-1.3%, 0.5%-1.4%, 0.5%-1.5%, 0.5%-1.6%, 0.5%-1.7%, 0.5%-1.8%, or 0.5%-1.9%, weight/weight cobalamins.

In some embodiments, a composition disclosed herein comprises, by way of non-limiting examples, 50-99.5%, 55-99.5%, 60-99.5%, 65-99.5%, 70-99.5%, 75-99.5%, 80-99.5%, 85-99.5%, 90-99.5%, 91-99.5%, 92-99.5%, 93-99.5%, 94-99.5%, 95-99.5%, 96-99.5%, 97-99.5%, 98-99.5%, or 99-99.5% weight/weight carrier.

Disclosed herein, in certain embodiments, are compositions, comprising: (a) methylcobalamin, hydroxocobalamin, and cyanocobalamin in substantially equivalent ratios, (b) a carrier suitable for forming solid or semi-solid carrier matrix, (c) a flavoring agent, and optionally, (d) a lubricant. Further disclosed herein are compositions, comprising: (a) methylcobalamin, hydroxocobalamin, and cyanocobalamin in substantially equivalent ratios, (b) isomalt, (c) PEG, (d) cherry flavoring, and, optionally, (e) magnesium stearate. Additionally disclosed herein are compositions, comprising: (a) methylcobalamin, hydroxocobalamin, and cyanocobalamin in substantially equivalent ratios, (b) isomalt, (c) PEG, (d) cherry flavoring, and (e) magnesium stearate.

The skilled artisan will appreciate that the combination of active ingredients found in the compositions described above also may be administered separately. In addition, the administration of one element may be prior to, concurrent to, or subsequent to the administration of other element(s).

Further, compositions of the present invention may be used in combination with other drugs that are used in the treatment/ prevention/suppression or amelioration of vitamin $B_{12}$ deficiencies or conditions. Such other drugs may be administered, by a route and in an amount commonly used therefore, contemporaneously or sequentially with a composition of the present invention. When a composition of the present invention is used contemporaneously with one or more other drugs or herbal supplements, vitamin supplements, etc., a pharmaceutical composition containing such other drugs in addition to the composition of the present invention is preferred. Accordingly, the pharmaceutical compositions of the present invention include those that also contain one or more other active ingredients, in addition to the compositions of the present invention.

Formulations

Disclosed herein in certain embodiments, are compositions, comprising: methylcobalamin, hydroxocobalamin, and cyanocobalamin in substantially equivalent ratios. In some embodiments, the composition further comprises a carrier suitable for forming solid or semi-solid carrier matrix. In other embodiments, the composition also comprises a lubricant. In some embodiments, the composition further comprises a flavoring agent. In some embodiments, the compositions are formulated for oral administration.

Disclosed herein, in certain embodiments, are compositions, comprising: (a) methylcobalamin, hydroxocobalamin, and cyanocobalamin in substantially equivalent ratios, (b) a carrier suitable for forming solid or semi-solid carrier matrix, (c) a flavoring agent, and optionally, (d) a lubricant; wherein the composition is formulated for oral and/or transmucosal administration. Further disclosed herein are compositions, comprising: (a) methylcobalamin, hydroxocobalamin, and cyanocobalamin in substantially equivalent ratios, (b) isomalt, (c) PEG, (d) cherry flavoring, and, optionally, (e) magnesium stearate; wherein the composition is formulated for oral and/or transmucosal administration. Additionally disclosed herein are compositions, comprising: (a) methylcobalamin, hydroxocobalamin, and cyanocobalamin in substantially equivalent ratios, (b) isomalt, (c) PEG, (d) cherry flavoring, and (e) magnesium stearate; wherein the composition is formulated for oral and/or transmucosal administration.

It is the primary object of the present invention to provide patient-friendly modes of delivery to patients of such effective amounts of vitamin $B_{12}$ analogues without the inconvenience and discomfort of subcutaneous and intramuscular injections. In accordance with the invention, vitamin $B_{12}$ is instilled in a carrier matrix, such as controlled-release lozenges, troches, tablets, hard or soft capsules, syrups or elixirs, pressed pills, gel caps, chewing gum, gels such as metered gels that can be administered intranasally, nasal drops, creams, lotions, aqueous or oily suspensions, dispersible powders or granules, emulsions, sprays or aerosols using flowing propellants, like liposomal sprays, nasal sprays, etc., douches and suppositories, transdermal patches, etc., all for patient-friendly, self-administration of effective amounts of vitamin $B_{12}$. The invention thereby minimizes inconvenience and discomfort for the patient and alleviates the burden and time demands imposed on medical staff. In some embodiments, the compositions disclosed herein are formulated for transdermal administration. In some embodiments, the compositions are formulated as lozenges, candies, tablets, wafers, films, sprays, gums, lip balms, or patches. The vitamin $B_{12}$ in formulations such as lozenges, troches, tablets, hard or soft capsules, gums, film, wafers, sprays, patches and lip balms, etc., are preferably absorbed directly via the mucosa, such as buccal, nasal mucosa, into the blood stream before being subjected to digestion and degradation in the liver. Preferred vitamin $B_{12}$ formulations include nasal gels, lozenges, including sublingual lozenges, nasal drops, nasal or pulmonary or other mucosal sprays, including liposomal sprays, fast absorbing capsules or tablets, gums, films, wafers, patches and lip balms.

Thus, the vitamin $B_{12}$ formulations of the present invention may be administered, but are not limited to, oral, parenteral (e.g., intramuscular, intraperitoneal, intravenous, ICV, intracisternal injection or infusion, subcutaneous injection, or implant), by inhalation spray, intranasal, transbuccal, mucosal, pulmonary, transdermal, liposomal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The pharmaceutical compositions for the administration of the compositions of this invention may conveniently be presented in dosage unit form and may be prepared by methods well known in the art of pharmacy. Suitable methods are described in, for example, Remington: The Science and Practice of Pharmacy, ed. Gennaro et al., 20th Ed. (2000), although the skilled artisan will recognize that other methods are known and are suitable for preparing the compositions of the present invention. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active ingredient is included in an effective amount, discussed above, sufficient to produce the desired effect upon the process or condition of diseases.

Tablets

In some embodiments, the compositions disclosed herein are formulated as tablets, e.g., fast dissolving tablets.

In some embodiments, the tablet is formulated to dissolve in 1 second to 30 minutes, 1 second to 25 minutes, 1 second to 20 minutes, 1 second to 15 minutes, 1 second to 14 minutes, 1 second to 13 minutes, 1 second to 12 minutes, 1 second to 11 minutes, 1 second to 10 minutes, 1 second to 9 minutes, 1 second to 8 minutes, 1 second to 7 minutes, 1 second to 6 minutes, 1 second to 5 minutes, 1 second to 4 minutes, 1 second to 3 minutes, 1 second to 2 minutes, 1 second to 1 minute, or 1 second to 30 seconds.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Capsules

In some embodiments, the compositions disclosed herein are formulated as capsules, e.g., hard capsules or soft capsules.

In some embodiments, the capsule is formulated to dissolve in 1 second to 30 minutes, 1 second to 25 minutes, 1 second to 20 minutes, 1 second to 15 minutes, 1 second to 14 minutes, 1 second to 13 minutes, 1 second to 12 minutes, 1 second to 11 minutes, 1 second to 10 minutes, 1 second to 9 minutes, 1 second to 8 minutes, 1 second to 7 minutes, 1 second to 6 minutes, 1 second to 5 minutes, 1 second to 4 minutes, 1 second to 3 minutes, 1 second to 2 minutes, 1 second to 1 minute, or 1 second to 30 seconds.

Wherein the composition is formulated as a hard capsule, in some embodiments, the composition is mixed with an inert solid diluent, for example, calcium carbonate, calcium phosphate or kaolin. Where the composition is formulated as a soft capsule, in some embodiments, the composition is mixed with water or an oil medium, for example peanut oil, liquid paraffin, or olive oil.

Lozenge

In some embodiments, the compositions disclosed herein are formulated as lozenges. In some embodiments, the lozenges may include hard lozenges, soft lozenges, gummy lozenges, or chewable lozenges.

In some embodiments, the lozenge is formulated to dissolve in 1 second to 30 minutes, 1 second to 25 minutes, 1 second to 20 minutes, 1 second to 15 minutes, 1 second to 14 minutes, 1 second to 13 minutes, 1 second to 12 minutes, 1 second to 11 minutes, 1 second to 10 minutes, 1 second to 9 minutes, 1 second to 8 minutes, 1 second to 7 minutes, 1 second to 6 minutes, 1 second to 5 minutes, 1 second to 4 minutes, 1 second to 3 minutes, 1 second to 2 minutes, 1 second to 1 minute, or 1 second to 30 seconds.

Candy

In some embodiments, the compositions disclosed herein are formulated as candies. In some embodiments, the candy may include hard candy, soft candy, gummy candy, or chewy candy.

In some embodiments, the candy is formulated to dissolve in 1 second to 30 minutes, 1 second to 25 minutes, 1 second to 20 minutes, 1 second to 15 minutes, 1 second to 14 minutes, 1 second to 13 minutes, 1 second to 12 minutes, 1 second to 11 minutes, 1 second to 10 minutes, 1 second to 9 minutes, 1 second to 8 minutes, 1 second to 7 minutes, 1 second to 6 minutes, 1 second to 5 minutes, 1 second to 4 minutes, 1 second to 3 minutes, 1 second to 2 minutes, 1 second to 1 minute, or 1 second to 30 seconds.

Film

In some embodiments, the compositions disclosed herein are formulated as films, e.g., dissolvable films. The film, by way of non-limiting example, is a clear or opaque, flexible, thin material.

The film-forming carrier used in the film formulations is selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

In some embodiments, the film is formulated to dissolve in 1 second to 30 minutes, 1 second to 25 minutes, 1 second to 20 minutes, 1 second to 15 minutes, 1 second to 14 minutes, 1 second to 13 minutes, 1 second to 12 minutes, 1 second to 11 minutes, 1 second to 10 minutes, 1 second to 9 minutes, 1 second to 8 minutes, 1 second to 7 minutes, 1 second to 6 minutes, 1 second to 5 minutes, 1 second to 4 minutes, 1 second to 3 minutes, 1 second to 2 minutes, 1 second to 1 minute, or 1 second to 30 seconds.

Gums

In some embodiments, the compositions disclosed herein are formulated as gums. In some embodiments, the gum may be non degradable chewing gum, degradable chewing gum, or liquid filled chewing gum.

In some embodiments, the gum formulations further comprise natural and synthetic elastomers and rubbers. For example, carriers suitable for a gum formulation include, but are not limited to, substances of vegetable origin such as chicle, jelutong, gutta percha and crown gum. Synthetic elastomers such as butadiene-styrene copolymers, isobutylene-isoprene copolymers, polyethylene, polyisobutylene and polyvinyl-acetate and mixtures thereof, are also useful.

In some embodiments, the elastomer solvent comprises methyl, glycerol or pentaerythritol esters of rosins or modified rosins, such as hydrogenated, dimerized or polymerized rosins, or mixtures thereof. Examples of elastomer solvents suitable for use herein include the pentaerythritol ester of partially hydrogenated wood rosin and partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and the partially hydrogenated methyl ester of rosin, such as polymers of alpha-pinene or beta-pinene, terpene resins including polyterpene and mixtures thereof.

A variety of traditional ingredients such as plasticizers or softeners such as lanolin, stearic acid, sodium stearate, potassium stearate, glyceryl triacetate, glycerine and the like, for example, natural waxes, petroleum waxes such as polyurethene waxes, paraffin waxes and microcrystalline waxes may also be incorporated into the gum formulations disclosed herein to obtain a variety of desirable textures and consistency properties.

Lip Balm

In some embodiments, the compositions disclosed herein are formulated as lip balms. In some embodiments, the lip balm may be in a tube, stick, or pot.

In some embodiments, the lip balm formulations further comprise a wax or other pharmaceutically acceptable vehicle, emollients, and oils.

Suitable waxes include animal waxes, plant waxes, mineral waxes, silicone waxes synthetic waxes and petroleum waxes. Exemplary specific waxes include, but are not limited to, carnauba wax; paraffin wax; white wax; candelilla wax; beeswax; jojoba wax; ozokerite; polyethylene; and combinations thereof.

In some embodiments, the lip balm formulations further comprise an oil or a butter, e.g., sunflower oil, coconut oil, castor oil, vegetable oil, corn oil, aloe vera oil, canola oil, soybean oil, jojoba oil, olive oil, babassu oil, avocado oil, apricot oil, meadowfoam seed oil, macadamia seed oil, oat kernel oil, palm seed oil, safflower oil, sandalwood oil, sesame oil, almond oil, wheat germ oil, cranberry oil, mango seed butter, raspberry butter, avocado butter, shea butter, olive butter, kuku butter, monoi butter, peach butter, pistachio butter, coconut butter, cocoa butter, pomegranate butter, rose hip butter, sunflower butter, wheat germ butter, apricot butter, babassu butter, cupuacu butter, kokum butter, hazelnut butter, jojoba butter, sesame butter, soy butter, almond butter, meadowfoam seed butter, black current seed butter and cranberry butter.

Buccal Patch

In some embodiments, the compositions disclosed herein are formulated as buccal patches. In some embodiments, the buccal patch, by way of non-limiting example, is a clear or opaque, flexible, thin material.

In some embodiments, the buccal patch is fabricated to dissolve gradually over a predetermined time period. In some embodiments, the buccal patch further comprises a bioerodible polymeric carrier, and any excipients that may be desired, e.g., penetration enhancers. As used herein, "bioerodible", i.e., the polymer hydrolyzes at a predetermined rate upon contact with moisture.

In some embodiments, the bioerodible polymeric carrier comprises a polymer having sufficient tack such that the patch adheres to the buccal mucosa for the time period necessary to produce the desired drug release profile. Generally, the polymeric carriers comprise hydrophilic (water soluble and water-swellable) polymers that adhere to the wet surface of the buccal mucosa. Examples of polymeric carriers useful herein include acrylic acid polymers and copolymers, e.g., those known as "carbomers" for example, Carbopol®. Other suitable polymers include, but are not limited to, hydrolyzed polyvinyl alcohol, polyethylene oxides (e.g., Sentry Polyox®), polyacrylates (e.g, Gantrez®), vinyl polymers and copolymers, polyvinylpyrrolidone, dextran, guar gum, pectins, starches, and cellulosic polymers such as hydroxypropyl methylcellulose (e.g., Methocel®), hydroxypropyl cellulose (e.g., Klucel®), hydroxypropyl cellulose; ethers, hydroxyethyl cellulose, sodium carboxymethyl cellulose, methyl cellulose, ethyl cellulose, cellulose acetate phthalate, cellulose acetate butyrate, and the like.

In some embodiments, the patch is formulated to dissolve in 1 second to 30 minutes, 1 second to 25 minutes, 1 second to 20 minutes, 1 second to 15 minutes, 1 second to 14 minutes, 1 second to 13 minutes, 1 second to 12 minutes, 1 second to 11 minutes, 1 second to 10 minutes, 1 second to 9 minutes, 1 second to 8 minutes, 1 second to 7 minutes, 1 second to 6 minutes, 1 second to 5 minutes, 1 second to 4 minutes, 1 second to 3 minutes, 1 second to 2 minutes, 1 second to 1 minute, or 1 second to 30 seconds.

Sprays

In some embodiments, the compositions disclosed herein are formulated as sprays. In some embodiments, the compositions disclosed herein are formulated as liposomal sprays. A liposome used for the preparation of the liposomal spray comprises of two lipid layers. The lipid layer may be a monolayer, or may be multilameliar and include multiple layers. In some embodiments, the liposome comprises phosphatidylcholine, but can include various natural (e.g., tissue derived L-oc-phosphatidyl: egg yolk, heart, brain, liver, soybean) and/or synthetic (e.g., saturated and unsaturated 1,2-diacyl-SN-glycero-3 15 phosphocholines, 1-acyl-2-acyl-SN-glycero-3-phosphocholines, 1,2 diheptanoyl-SN-glycero-3-phosphocholine) derivatives of the same. Such lipids can be used alone, or in combination with a helper lipid. Preferred helper lipids are non-ionic or uncharged at physiological pH.

Non-ionic lipids include, but are not limited to, cholesterol and DOPE (1,2-dioleolylglyceryl 20 phosphatidylethanolamine). Phosphatidic acid, which imparts an electric charge, may also be added.

In some embodiments, the spray is delivered by a metered dose pump. In other embodiments, the spray is delivered by mist spray pumps or squeeze bottles.

Miscellaneous

Formulations are also useful as dry powders or granules. Dispersible, dry powders are useful for inhalation after aerosolization with a suitable dispersion device. Dry powder dispersion devices for medicaments are described in a number of patent documents. U.S. Pat. No. 3,921,637 describes a manual pump with needles for piercing through a single capsule of powdered medicine. The use of multiple receptacle disks or strips of medication is described in EP 467172 (where a reciprocatable piercing mechanism is used to pierce through opposed surfaces of a blister pack); WO91/02558; WO93/09832; WO94/08522; U.S. Pat. Nos. 4,627,432; 4,811,731; 5,035,237; 5,048,514; 4,446,862; and 3,425,600. Other patents which show puncturing of single medication capsules include U.S. Pat. Nos. 4,338,931; 3,991,761; 4,249,526; 4,069,819; 4,995,385; 4,889,114; and 4,884,565; and EP 469814. WO90/07351 describes a hand-held pump device with a loose powder reservoir. Further dry powder dispensers are also covered in U.S. Pat. No. 6,089,228 which specifically provides an improved apparatus for aerosolizing a powdered medicament, hereby incorporated by reference.

Dispersible powders and granules are also suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. Syrups and elixirs may be formulated with sweetening agents, for example glycerol, propylene glycol, sorbitol or sucrose. Such formulations may also contain a demulcent, preservative, flavoring and coloring agent.

The pharmaceutical compositions may sometimes be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, gels including nasal gels, ointments, jellies, solutions or suspensions, mouth washes and gargles, etc., containing the compositions of the present invention, are employed.

Disorders and Conditions Related to Vitamin $B_{12}$ Deficiency

Disclosed herein in certain embodiments, are compositions, comprising: methylcobalamin, hydroxocobalamin, and cyanocobalamin in substantially equivalent ratios. In some embodiments, the composition further comprises a carrier suitable for forming a solid or semi-solid carrier matrix. In other embodiments, the composition also comprises a lubricant. In some embodiments, the composition further comprises a flavoring agent. In some embodiments, the compositions are formulated for oral administration.

Disclosed herein, in certain embodiments, are compositions, comprising: (a) methylcobalamin, hydroxocobalamin, and cyanocobalamin in substantially equivalent ratios, (b) a carrier suitable for forming solid or semi-solid carrier matrix, (c) a flavoring agent, and optionally, (d) a lubricant; wherein the composition is formulated for oral and/or transmucosal administration. Further disclosed herein are compositions, comprising: (a) methylcobalamin, hydroxocobalamin, and cyanocobalamin in substantially equivalent ratios, (b) isomalt, (c) PEG, (d) cherry flavoring, and, optionally, (e) magnesium stearate; wherein the composition is formulated for oral and/or transmucosal administration. Additionally disclosed herein are compositions, comprising: (a) cyanocobalamin, hydroxocobalamin, and methylcobalamin in substantially equivalent ratios, (b) isomalt, (c) PEG, (d) cherry flavoring, and (e) magnesium stearate; wherein the composition is formulated for oral and/or transmucosal administration.

The following diseases, disorders and conditions are related to vitamin $B_{12}$ deficiency, and therefore may be treated, controlled or in some cases prevented, by treatment with the composition of this invention: pernicious anemia; ataxia; autoimmune disorders; patients receiving long term therapy with gastric acid inhibitors like biguanides; patients with atrophic body gastritis, or who have had partial or total gastrectomy; anemia associated with drug-therapy (for example, methotrexate, metformin, phenobarbital, phenytoin, etc.; alcohol or substance abuse; inflammation of joints; arthritis; burns; neurodegenerative disease like Alzheimer's disease, amyotrophic lateral sclerosis or multiple sclerosis; senior dementia; allergic diseases such as rhinitis, allergic asthma, etc.; HIV/AIDS where there poor absorption of vitamin $B_{12}$; irritable bowel syndrome or patients who have undergone intestinal surgery; inflammatory bowel disease, including Crohn's disease and ulcerative colitis; suppression of IgE production; and other disorders where vitamin $B_{12}$ deficiency is a component.

In some embodiments, vitamin $B_{12}$ deficiency is associated with anemia. In some embodiments, the vitamin $B_{12}$ deficiency is associated with pernicious anemia. In some embodiments, the vitamin $B_{12}$ deficiency is associated with a disease, selected from: Graves' disease, hypothyroidism, thyroiditis, vitiligo, Addison's disease, atrophic gastritis, or thrombocytopenia. In some embodiments, the vitamin $B_{12}$ deficiency is associated with an immune disorder, selected from: amyotrophic lateral sclerosis, multiple sclerosis, Crohn's disease, Celiac disease, ulcerative colitis, Alzheimer's disease, AIDS, joint inflammation, or arthritis. In some embodiments, the vitamin $B_{12}$ deficiency is associated with administration of a drug known to impair absorption of vitamin $B_{12}$, wherein the drug known to impair absorption of vitamin $B_{12}$ is selected from: gastric acid inhibitors, biguanides, proton pump inhibitors, $H_2$ receptor antagonists, metformin, or chloramphenicol. In some embodiments, the vitamin $B_{12}$ deficiency is associated with ataxia. In some embodiments, the vitamin $B_{12}$ deficiency is associated with partial removal of the stomach or small intestine. In some embodiments, the vitamin $B_{12}$ deficiency is associated with alcoholism. In some embodiments, the vitamin $B_{12}$ deficiency is associated with Alagille's syndrome, severe methylenetetrahydrofolate reductase deficiency, homocystinuria, or transcobalamin deficiency.

Kits

Disclosed herein in certain embodiments, are kits, comprising a composition comprising: methylcobalamin, hydroxocobalamin, and cyanocobalamin in substantially equivalent ratios. In some embodiments, the composition further comprises a carrier suitable for forming solid or semi-solid carrier matrix. In other embodiments, the composition also comprises a lubricant. In some embodiments, the composition further comprises a flavoring agent. In some embodiments, the compositions are formulated for oral administration.

Disclosed herein, in certain embodiments, are kits, comprising compositions comprising: (a) methylcobalamin, hydroxocobalamin, and cyanocobalamin in substantially equivalent ratios, (b) a carrier suitable for forming solid or semi-solid carrier matrix, (c) a flavoring agent, and optionally, (d) a lubricant; wherein the composition is formulated for oral and/or transmucosal administration. Further disclosed herein are kits, comprising compositions comprising: (a) methylcobalamin, hydroxocobalamin, and cyanocobalamin in substantially equivalent ratios, (b) isomalt, (c) PEG, (d) cherry flavoring, and, optionally, (e) magnesium stearate; wherein the composition is formulated for oral and/or transmucosal administration. Additionally disclosed herein are kits, comprising compositions comprising: (a) methylcobalamin, hydroxocobalamin, and cyanocobalamin in substantially equivalent ratios, (b) isomalt, (c) PEG, (d) cherry flavoring, and (e) magnesium stearate; wherein the composition is formulated for oral and/or transmucosal administration.

In certain embodiments, the kits comprise a composition disclosed herein and instructions for storage, administration, dosing, and disease state for which the formulation is useful, etc. In yet another embodiment is an article of manufacture comprising a composition or formulation disclosed herein and an apparatus to dispense or administer the formulation to a given patient, such as a container for housing the composition, etc.

In some embodiments, the kits described herein include the composition described herein, and instructions for using the kit. In further embodiments, the kits include packaging materials including, but not limited to, blister packs, bottles, tubes, inhalers, pumps, bags, vials, containers, bottles, and any packaging material suitable for a selected formulation and intended mode of administration and treatment, including labels listing contents and/or instructions for use, and package inserts, with instructions for use. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the composition is presented in a pack or dispenser device which contains one or more unit dosage forms containing a composition provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound disclosed herein formulated in a compatible pharmaceutical carrier are also prepared, placed in an appropriate container, and labeled for treatment of an indicated condition.

EXAMPLES

Example 1

Composition

A lozenge is prepared. The components of the composition, and their respective amounts, by weight, are listed in Table 1.

TABLE 1

| Material | Milligram per Unit Dose |
| --- | --- |
| Cyanocobalamin, Hydroxocobalamin, Methylcobalamin | Equal amounts of each |
| Isomalt galenIQ ™ 721 | 182.750 |
| Polyethylene Glycol 8000 | 62.500 |
| Flavoring | 0.500 |
| Magnesium Searate | 1.250 |

Example 2

Manufacture of Vitamin $B_{12}$ Composition

About 5 grams of cyanocobalamin, about 5 grams of hydroxycobalamin acetate and about 5 grams of methylcobalamin are passed through a #20 mesh stainless steel screen.

About 15 grams of isomalt is passed through a #20 mesh screen and combined with the methyl-, cyano- and hydroxycobalamin mixture. Pre-blend 1 is mixed until a substantially homogenous mixture is observed.

About 90 grams of isomalt is passed through a #20 mesh screen and combined with pre-blend 1. Pre-blend 2 is mixed until a substantially homogenous mixture is observed.

About 360 grams of isomalt is passed through a #20 mesh screen and combined with pre-blend 2. Pre-blend 3 is mixed until a substantially homogenous mixture is observed. Pre-blend 3 is transferred into a blender.

About 448.75 grams of isomalt, about 312.5 grams of PEG-8000 and about 2.5 grams of cherry flavoring are passed through a #20 mesh screen and transferred into the blender with pre-blend 3 and blended until substantially homogenous to generate blend 1.

About 6.250 grams of magnesium stearate is passed through a #20 mesh screen and combined with blend 1 in the blender and blended until substantially homogenous to generate blend 2.

Blend 2 is divided into unit dosages and each unit dosage is compressed into a tablet.

Example 3

Treating Vitamin $B_{12}$ Deficiency with Vitamin $B_{12}$ Described herein

A human presents with vitamin $B_{12}$ deficiency associated with pernicious anemia, including impaired perception of deep touch and deep muscle-tendon reflexes. The patient self-administers a vitamin $B_{12}$ lozenge according to Example 1. The human's symptoms of vitamin $B_{12}$ deficiency are decreased.

What is claimed is:

1. A sublingual composition, consisting essentially of:
   a. cyanocobalamin, hydroxocobalamin, and methylcobalamin in substantially equivalent ratios;
   b. a carrier suitable for forming a solid or semi-solid carrier matrix, consisting essentially of isomalt and polyethylene glycol (PEG);
   c. a flavoring agent; and
   d. a lubricant.

2. The composition of claim 1, wherein the PEG is PEG-8000.

3. The composition of claim 1, wherein the lubricant is magnesium stearate.

4. The composition of claim 1, wherein the flavoring agent is cherry.

5. The composition of claim 1, wherein the composition is formulated as a lozenge, a candy, a wafer, a tablet, a patch, a film, or a spray.

6. The composition of claim 5, wherein the composition is formulated as a lozenge.

7. A method for treating or ameliorating vitamin $B_{12}$ deficiency in a human in need thereof, comprising: administering to the human the composition of claim 1.

8. The method of claim 7, wherein the vitamin $B_{12}$ deficiency is associated with anemia, Graves' disease, hypothyroidism, thyroiditis, vitiligo, Addison's disease, atrophic gastritis, thrombocytopenia, amyotrophic lateral sclerosis, multiple sclerosis, Crohn's disease, Celiac disease, ulcerative colitis, Alzheimer's disease, AIDS, joint inflammation, arthritis, ataxia, partial removal of the stomach or small intestine, alcoholism, Alagille's syndrome, severe methylenetetrahydrofolate reductase deficiency, homocystinuria, or transcobalamin deficiency, or any combinations thereof.

9. The method of claim 8, wherein the vitamin $B_{12}$ deficiency is associated with pernicious anemia.

10. The method of claim 7 wherein the vitamin $B_{12}$ deficiency is associated with administration of drugs known to impair absorption of vitamin $B_{12}$.

11. The method of claim 10, wherein the drug known to impair absorption of vitamin $B_{12}$ is: a gastric acid inhibitor, a biguanide, a proton pump inhibitor, an $H_2$ receptor antagonist.

12. The method of claim 10, wherein the drug known to impair absorption of vitamin $B_{12}$ is metformin, chloramphenicol, methotrexate, or any combination.

13. A kit comprising: the composition of claim 1.

* * * * *